(12) United States Patent
Zeegers

(10) Patent No.: US 9,566,164 B2
(45) Date of Patent: *Feb. 14, 2017

(54) INTERVERTEBRAL DISC PROSTHESIS

(71) Applicant: LDR MEDICAL, Rosières Près Troyes (FR)

(72) Inventor: Willem Zeegers, EJ Meerseen (NL)

(73) Assignee: LDR Medical, Sainte-Savine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/726,557

(22) Filed: May 31, 2015

(65) Prior Publication Data
US 2015/0257895 A1   Sep. 17, 2015

Related U.S. Application Data

(63) Continuation of application No. 13/603,043, filed on Sep. 4, 2012, now Pat. No. 9,044,339, which is a continuation of application No. 12/360,050, filed on Jan. 26, 2009, now Pat. No. 8,257,439, which is a
(Continued)

(30) Foreign Application Priority Data

Dec. 22, 2004   (FR) ..................... 04 13728

(51) Int. Cl.
*A61F 2/44* (2006.01)
*A61B 17/064* (2006.01)
*A61F 2/30* (2006.01)

(52) U.S. Cl.
CPC ......... *A61F 2/4425* (2013.01); *A61B 17/0642* (2013.01); *A61F 2/30721* (2013.01); *A61F 2/30749* (2013.01); *A61F 2/442* (2013.01); *A61F 2/30734* (2013.01); *A61F 2002/305* (2013.01); *A61F 2002/3038* (2013.01); *A61F 2002/30365* (2013.01); *A61F 2002/30369* (2013.01); *A61F 2002/30387* (2013.01); *A61F 2002/30471* (2013.01); *A61F 2002/30517* (2013.01); *A61F 2002/30576* (2013.01); *A61F 2002/30616* (2013.01); *A61F 2002/30662* (2013.01); *A61F 2002/30729* (2013.01); *A61F 2002/30884* (2013.01); *A61F 2002/443* (2013.01);
(Continued)

(58) Field of Classification Search
CPC ..................................... A61F 2/4425
See application file for complete search history.

(56) References Cited

U.S. PATENT DOCUMENTS

| 2005/0060034 A1* | 3/2005 | Berry | A61F 2/4425 623/17.11 |
| 2005/0149189 A1* | 7/2005 | Mokhtar | A61F 2/4425 623/17.11 |
| 2005/0228500 A1* | 10/2005 | Kim | A61F 2/442 623/17.13 |

FOREIGN PATENT DOCUMENTS

WO   WO 2004/041129   * 5/2004   ........... A61F 2/4425

* cited by examiner

*Primary Examiner* — Andrew Yang
(74) *Attorney, Agent, or Firm* — Lauff Law PLLC

(57) ABSTRACT

The present invention relates to an intervertebral disc prosthesis comprising at least three pieces including an upper plate, a lower plate, and a movable core at least in relation to a plate, wherein it also comprises two anatomic adaptation elements of which each has, on one hand, a surface in contact with a surface of a vertebra and, on the other hand, a face of which at least a part has a surface in contact with at least a part of the plate opposite to which the anatomic adaptation element is mounted, the anatomic adaptation elements being fixed onto the plates via fixation means.

15 Claims, 11 Drawing Sheets

Related U.S. Application Data continuation of application No. 11/109,276, filed on Apr. 18, 2005, now Pat. No. 7,695,516.

(52) U.S. Cl.
CPC ........... *A61F 2220/0025* (2013.01); *A61F 2220/0033* (2013.01); *A61F 2220/0091* (2013.01)

I - I ns a continuation of U.S. application Ser. No. 13/603,043 filed Sep. 4, 2012, and issuing as U.S. Pat. No. 9,044,339 on Jun. 2, 2015, which is a continuation of U.S. application Ser. No. 12/360,050 filed Jan. 26, 2009, and issuing as U.S. Pat. No. 8,257,439 on Sep. 4, 2012, which is a continuation of U.S. application Ser. No. 11/109,276, filed Apr. 18, 2005, and issuing as U.S. Pat. No. 7,695,516 on Apr. 13, 2010, which claims priority to French Patent Application No. 0413728, filed in FRANCE on Dec. 22, 2004, respectively, and the contents of these prior applications are incorporated herein by reference in their entirety.

BACKGROUND

The present invention relates to an intervertebral disc prosthesis, intended to be substituted for fibro-cartilaginous discs ensuring a bond between the vertebrae of the spinal column.

Various types of intervertebral disc prostheses are known in the prior art. Numerous prostheses, such as for example in the patent application WO 02 089 701 and WO 2004/041129, are constituted in a lower plate and an upper plate forming a sort of cage around a central core. A part of these prostheses enables the upper plate to swivel in relation to the central core and optionally permits the central core to slide in relation to the lower plate. This sliding of the central core in relation to the lower plate allows spontaneous positioning of the core in the ideal position to absorb constraints imposed on the prosthesis, during movements made by the patient wearing the prosthesis. The displacement of the core, co-operating with at least a plate about an uneven surface, enables an inclination between the plates of the prosthesis which facilitates the mobility of the patient wearing the prosthesis. The displacement of the core also prevents it from creeping under load, when subjected to major constraints. A part of these prostheses have osseous anchorage means allowing to attach these prostheses to the vertebrae between which they are intended to be inserted.

However, the size of the vertebrae varies greatly from person to person, for a same vertebra in a given position in the spinal column, but also for a given person depending on the position of the vertebrae in the spinal column between which a prosthesis is intended to be inserted. The intervertebral disc prostheses must be of a suitable size for the vertebrae between which they are intended to be inserted, depending on the person and on the position of these vertebrae in the spinal column. Moreover, depending on the spinal column disorder of the patient wearing the prosthesis, it is sometimes preferable that the prosthesis allows a correction of this disorder. The prostheses can thus be used to correct an inclination defect of the vertebrae, such as, for example, lordosis. To have prostheses that are suitable for as large a majority of cases as possible, many different prostheses with different plate sizes and inclinations must therefore be envisaged. This multiplicity of prostheses has the major inconvenience of high manufacturing costs and high stock levels. In this context, it is beneficial to provide a prosthesis that may be adapted to different sizes of vertebrae while allowing for different inclinations of the plates. Such a prosthesis would reduce stock levels and manufacturing costs.

One object of the present invention is to provide an intervertebral disc prosthesis allowing limited movements of the different pieces of the prosthesis between one another and comprising a core used to restrict its displacement in at least one direction.

This aim is achieved by an intervertebral disc prosthesis comprising at least three pieces including an upper plate, a lower plate, and a movable core at least in relation to a plate, having two anatomic adaptation elements each of which has, on one hand, a surface in contact with a surface of a vertebra and, on the other hand, a surface of which at least a part of has a surface in contact with at least a part of the plate opposite to which the anatomic adaptation element is mounted, the anatomic adaptation elements being fixed onto the plates via fixation means.

In other embodiments, the anatomic adaptation elements include crowns which surround the plates and prolong respectively their upper and lower surfaces to present contact surfaces of the prosthesis with the adjacent vertebrae are larger. In other embodiments, the crowns of the anatomic adaptation elements of various sizes are adapted on the plates in order to adapt them to vertebrae of different sizes.

According to another feature of some embodiments, the anatomic adaptation elements are anatomic plates, which cover the plates and prolong respectively their upper and lower surfaces to present contact surfaces of the prosthesis with the adjacent vertebrae which are bigger than when there are no anatomic adaptation elements, the anatomic plates being of various sizes in various embodiments to adapt the plates to vertebrae of different sizes.

According to another feature of some embodiments, the anatomic adaptation elements act to effectively and symmetrically prolong the upper and lower surfaces respectively of the upper and lower plates to present an equivalent prolongation of these surfaces on the different anterior, posterior and lateral edges of the plates.

According to another feature of some embodiments, the anatomic adaptation elements act to effectively and asymmetrically prolong the upper and lower surfaces respectively of the upper and lower plates to present a bigger prolongation of these surfaces on at least one of the anterior, posterior and lateral edges of the plates than on the other edges.

According to another feature of some embodiments, the upper surface of the core is in contact with at least one part of the lower surface of the upper plate and the lower surface of the core is in contact with at least one part of the upper surface of the lower plate.

According to another feature of some embodiments, at least one part of the surface of at least a plate is concave and complementary with a convex surface of the core with which it is in contact.

According to another feature of some embodiments, at least one part of the surface of at least a plate is plane and complementary with a plane surface of the core with which it is in contact.

According to another feature of some embodiments, male and female cooperation means situated in the vicinity of the edges of at least one plate and the core limit preferably, without excessive friction, the movements in translation of the core relative to the selected plate, according to an axis substantially parallel to selected plate, and limit or suppress the rotational movement of the core relative to the selected plate, about an axis substantially perpendicular to the selected plate.

According to another feature of some embodiments, the dimensions of each male cooperation means are slightly less than those of each female cooperation means so as to allow clearance between the core and the plate in embodiments equipped with these cooperation means.

According to another feature of some embodiments, the dimensions of each male cooperation means are substantially the same as those of each female cooperation means so as to prevent any clearance between the core and the plate equipped with these cooperation means.

According to another feature of some embodiments, the cooperation means of the plate are female cooperation means co-operating with male cooperation means of the core.

According to another feature of some embodiments, the male cooperation means of the core are two blocks situated on the two side edges of the core and the female cooperation means of the plate are four walls situated, in pairs, on each of the two side edges of this plate.

According to another feature of some embodiments, the fixation means of the anatomic adaptation elements on the plates of the prosthesis are reversible and allow changing the anatomic adaptation elements fixed in a movable manner onto the plates of the prosthesis.

According to another feature of some embodiments, the fixation means of the anatomic adaptation elements on the plates consist in fixation means present on the anatomic adaptation elements and complementary with fixation means present on the plates of the prosthesis.

According to another feature of some embodiments, the anatomic adaptation elements are fixed onto the plates via, on one hand, contact with at least a part of their surfaces which face at least a part of the plates and, on the other hand, contact of their fixation means with the complementary fixation means present on the plates of the prosthesis.

According to another feature of some embodiments, the fixation means of the anatomic adaptation elements on the plates consist in male fixation means present on the anatomic adaptation elements and that cooperate with the female fixation means present on the plates of the prosthesis or inversely.

According to another feature of some embodiments, the female fixation means present on the plates of the prosthesis consist of plane surfaces present on the edges of the plates of the prosthesis.

According to another feature of some embodiments, the female fixation means present on the plates of the prosthesis consist of recesses made in the edges of the other plate of the prosthesis.

According to another feature of some embodiments, the female fixation means present on the plates of the prosthesis consist of recesses made in the edges of the female cooperation means of the plates of the prosthesis.

According to another feature of some embodiments, the female fixation means present on the plates of the prosthesis consist of plane surfaces present on the edges of one of the plates and in recesses made in the female cooperation means of the edges of the other plate of the prosthesis.

According to another feature of some embodiments, the female fixation means present on at least one of the plates of the prosthesis consist of plane surfaces present on at least a first edge of one of the plates and in recesses made in at least a second edge of the plate of the prosthesis, the second edge geometrically facing a first edge of the plate.

According to another feature of some embodiments, at least one of the female fixation means present on the plates of the prosthesis comprises at least a notch allowing blocking the male fixation means of the anatomic adaptation elements on the selected female fixation means.

According to another feature of some embodiments, the fixation means of the anatomic adaptation elements on the plates consist of female fixation means present on the anatomic adaptation elements and co-operating with male intermediary means which can also cooperate with the female fixation means present on the plates of the prosthesis.

According to another feature of some embodiments, the anatomic adaptation elements are fixed onto the plates via, on one hand, contact of at least a part of their upper and lower surface with at least a part of respectively the upper and lower plates and, on the other hand, contact of the male intermediary means with the female fixation means present on the anatomic adaptation elements and with the female fixation means present on the plates of the prosthesis.

According to another feature of some embodiments, the male intermediary means possess securing means fixing the male intermediary means in a position to cooperate with both the female fixation means of the anatomic adaptation elements and the female fixation means present on the plates of the prosthesis.

According to another feature of some embodiments, the male intermediary means consist of a sliding plate in the female fixation means present on the anatomic adaptation elements to cooperate with the female fixation means present on the plates of the prosthesis, the securing means of the male intermediary means consisting of at least an irregularity present on at least one side of the selected plate that cooperates with an opening in the female fixation means of the anatomic adaptation elements and/or in the female fixation means of the plates, thus fixing the male intermediary means in a position where they cooperate with both the female fixation means of the anatomic adaptation elements and the female fixation means present on the plates of the prosthesis.

According to another feature of some embodiments, the securing means of the male intermediary means consist of a bore in the male intermediary means and in the female fixation means present on the anatomic adaptation elements, the bore in the female fixation means of the anatomic adaptation elements capable of receiving a securing pin fixing the male intermediary means in the position to cooperate with the female fixation means present on the plates of the prosthesis.

According to another feature of some embodiments, the median planes representing the upper and lower surfaces of each of the anatomic adaptation elements are substantially parallel or form an acute angle, the inclination obtained by such an angle allowing adaptation of the overall shape of the prosthesis to the anatomy of the spinal column and in some embodiments ameliorate inclination defects of the vertebrae of the patient for whom the prosthesis is intended.

According to another feature of some embodiments, the same anatomic adaptation elements may be assembled with different plates whose upper and lower surfaces create different angles.

According to another feature of some embodiments, an angle between the upper surface of the upper plate and the lower surface of the lower plate is imposed by creation of angles between the upper and lower surfaces of the lower plate and/or the upper plate, or by restricting, with the cooperation means, movements of the core about a position imposing an inclination of at least one of the plates.

According to another feature of some embodiments, the same plates are assembled with cores of different thicknesses and/or sizes and/or shapes.

According to another feature of some embodiments, the anatomic adaptation elements comprise movable osseous anchorage elements that are fixed onto the anatomic adaptation elements upon fixing the anatomic adaptation elements onto the plates, inserting the prosthesis between the vertebrae or adjusting the relative position of the different elements of the prosthesis.

According to another feature of some embodiments, the movable osseous anchorage elements of the anatomic adaptation elements consist of at least a plate equipped with notches oriented to resist the removal of the plate once it has been inserted into a vertebra, a far end of the plate bearing a part curved to fold over itself that may interlock as a hook onto an edge of an opening made in the vicinity of the periphery of the anatomic adaptation elements.

According to another feature of some embodiments, the part, curved to fold over itself, of the notched plate of the movable osseous anchorage means of the anatomic adaptation elements in prolonged with a second plate also equipped with notches oriented to resist removal once it has been inserted into the vertebra.

According to another feature of some embodiments, the anatomic adaptation elements comprise movable osseous anchorage elements consisting of at least one winglet that may be inserted in a groove formed in the adjacent surfaces of the vertebrae between which the prosthesis is to be implanted, said winglet comprising notches oriented to resist ejection of the prosthesis outside its housing between the vertebrae, a far end of the winglet bearing a part curved to fold over itself that may be interlocked as a hook onto an edge of an opening made in the vicinity of the periphery of the anatomic adaptation elements.

According to another feature of some embodiments, the winglet further comprises a pin having dimensions adapted to fit preferably tightly, into a groove of the anatomic adaptation elements and/or the plates.

BRIEF DESCRIPTION OF THE FIGURES

Other features and advantages of the invention will emerge more clearly from the description herein below, given in reference to the attached diagrams, in which.

DETAILED DESCRIPTIONS

Figure 1:
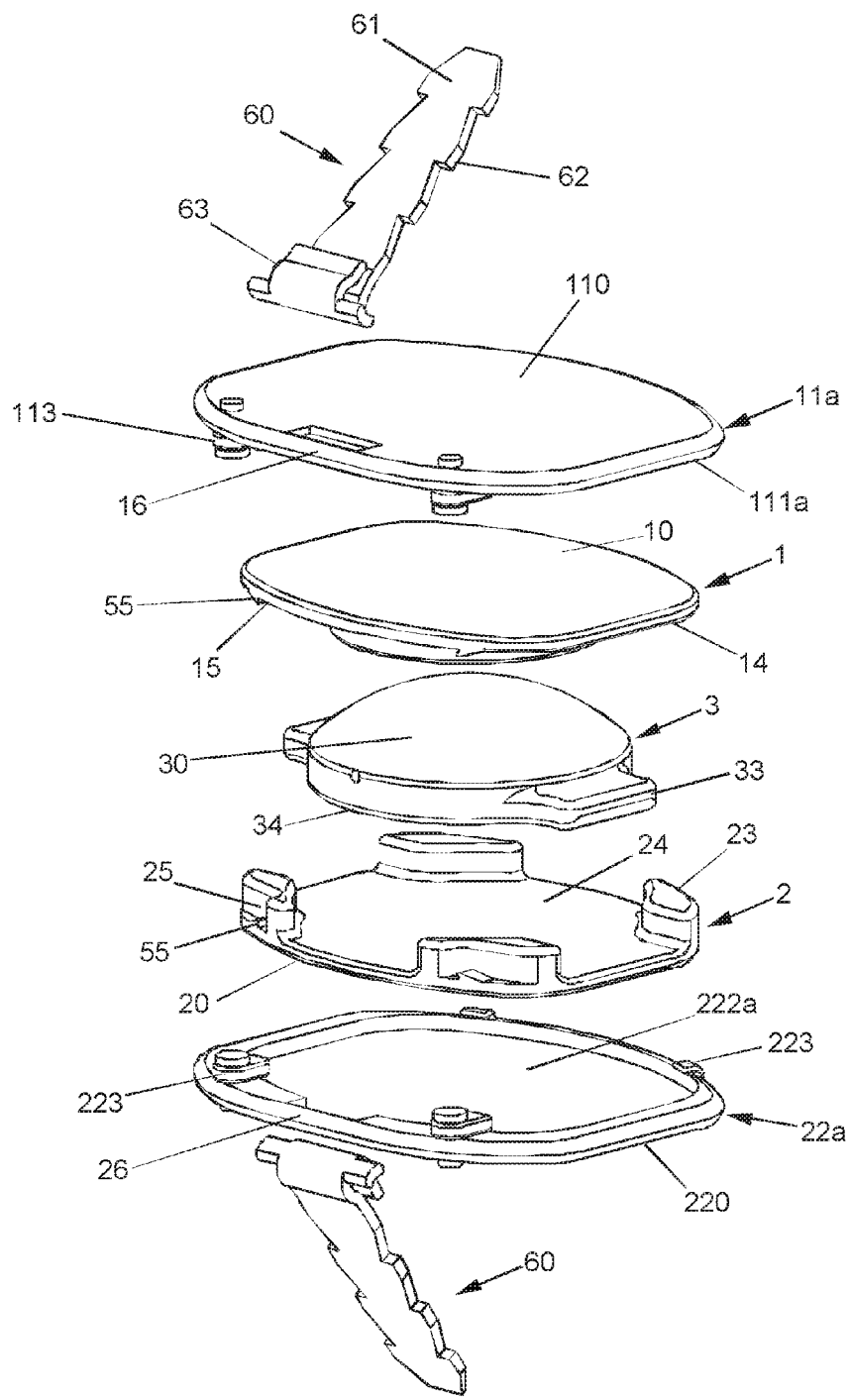
FIG. 1 illustrates an exploded perspective view of the different elements of the prosthesis according to an embodiment of the invention.

The intervertebral disc prosthesis according to the present invention has an upper plate (1) articulated in relation to a lower plate (2) by means of a core (3). Each of the plates (1, 2) is equipped with an anatomic adaptation element (11, 22) allowing adjustment of the overall size of the prosthesis to the size of the vertebrae. Thus the variable size adaptability reduces the cost of manufacturing prostheses and their varieties. One advantage of the prosthesis according to the invention is that it comprises simple parts whose anatomic adaptation elements (11, 22) can be sized so as to adapt to different vertebrae of the spinal column. For example, the thickness of the prosthesis may be adjusted to the intervertebral gap and/or the inclination of the plates (1, 2) of the prosthesis may be adapted to the inclination of the vertebrae of the patient. Even though the anatomic adaptation elements (11, 22) allow adjustment of the prosthesis to different sizes of vertebrae, plates (1, 2) and core (3) of differing sizes and shapes can be used where desired.

Anatomic adaptation elements (11, 22) of the prosthesis (for example, plates 11a and 22a or crowns 11b or 22b) include an upper element (11) and a lower element (22). Upper element (11) has, an upper surface (110) of which at least a part presents a surface in contact with a lower surface of a first vertebra and, a lower surface (111a) or lower edge (111b) at least a part of which presents a surface in contact with a part of upper plate (1). Lower element (22) has a lower surface (220), at least a part of which presents a surface in contact with an upper surface of a second vertebra and has, an upper surface (222a) or upper edge (222b) at least a part of which presents a surface in contact with a part of the lower plate (2). Each of the two anatomic adaptation elements (11, 22) is fixed onto the plates (1, 2) via respective fixation means (113, 223).

The core (3) of various embodiments varies in thickness from approximately 3 to 15 mm, depending on the vertebrae between which the prosthesis is to be inserted. Core (3) may in some embodiments, for example, be made of polyethylene, a compressible material simulating the physical properties of elasticity of natural intervertebral discs.

In some embodiments of the invention, core (3) has a convex part on at least a part of at least one of its upper (30) and lower (34) surfaces. In the embodiments illustrated in FIGS. 1 to 9, it is the upper surface (30) of the core (3) which is convex and complementary with a concave part (140) of the lower surface (14) of the upper plate (1), whereas the lower surface (34) of the core (3) is plane and complementary with at least a plane part of the upper surface (24) of the lower plate (2). The concave part (140) of the lower surface (14) of the upper plate (1), as particularly visible in FIGS. 4A, 4B, 5A, 5B and 5C, has a circular periphery. In other possible embodiments (not shown), a part of the lower surface (34) of the core (3) may be convex and complementary with a concave part of the upper surface (24) of the lower plate (2), whereas the upper surface (30) of the core (3) is plane and complementary with at least a plane part of the lower surface (14) of the upper plate (1). In other embodiments (not shown), the concave surface lies on a part of one of the upper (30) and lower (34) surfaces of the core (3) and cooperates with a convex surface which lies on a part of a surface of one of the plates (1, 2). In some different embodiments (not shown), the non convex or non concave surface of the core (3) can respectively be concave or convex, to a slight degree.

In the embodiments illustrated in FIGS. 1 to 9, the concave part (140) of the lower surface (14) of the upper plate (1) complementary with the convex part of the upper surface (34) of the core (3) allows inclination of the upper plate (1) when the patient wearing the prosthesis bends over. The cooperation between the concave surface (140) and the convex surface (34) presents a surface of articulation with the prosthesis, due to this inclination of the upper plate (1) in relation to the core (3). The center of this articulation is typically at the tip of the convex surface (34) of the core (3). In the illustrated embodiments, the lower surface of the core (3) and the upper surface of the lower plate (2) are plane so as to permit clearance of the core (3) in relation to the lower plate (2), both in translation according to an axis substantially parallel to the lower plate (2), and in rotation about an axis substantially perpendicular to the lower plate (2). During movement by the patient wearing the prosthesis, this inclination of the upper plate (1) and this clearance of the core will allow displacement of the core (3) towards the ideal position to absorb the constraints applied to the prosthesis. The movement between the upper plate (1) and the core (3), as well as the clearance of the core (3) in relation to the lower plate (2) thus allow the patient to move, and, optionally, to eliminate the defects of positioning the prosthesis. This clearance likewise has the advantage of preventing premature wear due to the constraints applied to the prosthesis.

The core (3) also has male or female cooperation means (33) complementary with respectively female or male cooperation means (23) present on at least one of the plates (1, 2). These male and female cooperation means (23, 33) situated in the vicinity of the edges of at least one plate (1, 2) and of the core (3) limit, preferably without excessive friction, movements in translation of the core (3) in relation to this plate (1, 2), according to an axis substantially parallel to this plate (1, 2), and limit or suppress the movements in rotation of the core (3) in relation to this plate (1, 2), about an axis substantially perpendicular to this plate (1, 2). The dimensions of each male cooperation means (33) may be slightly less than those of each female cooperation means (23) so as to allow slight clearance between the core (3) and the plate (1, 2) equipped with these cooperation means. The dimensions of each male cooperation means (33) may also be substantially the same as those of each female cooperation means (23) so as to prevent any clearance between the core (3) and the plate (1, 2) equipped with these cooperation means.

Figure 2:
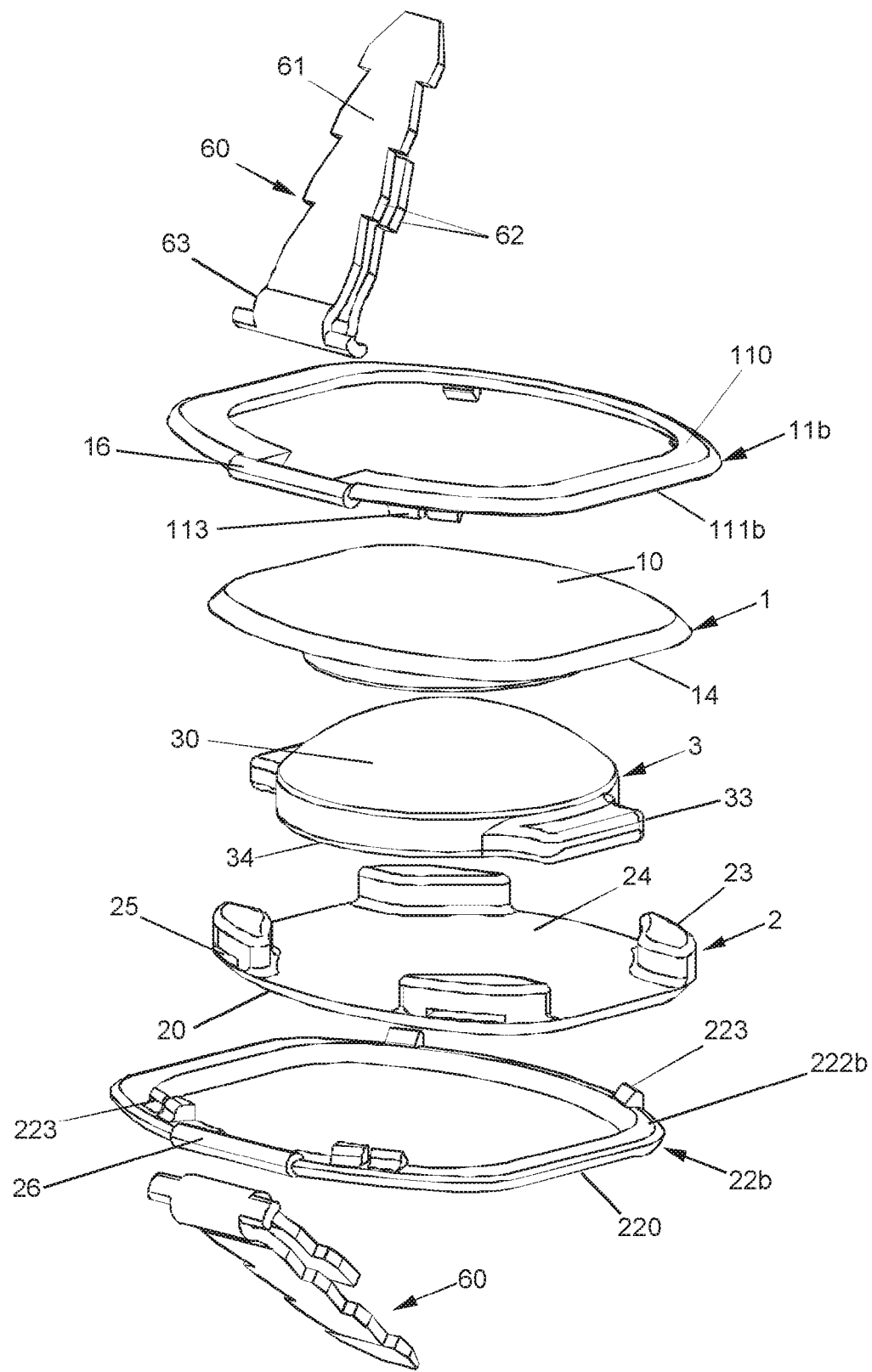
FIG. 2 illustrates an exploded perspective view of the different elements of the prosthesis according to another embodiment of the invention.
Figure 3:
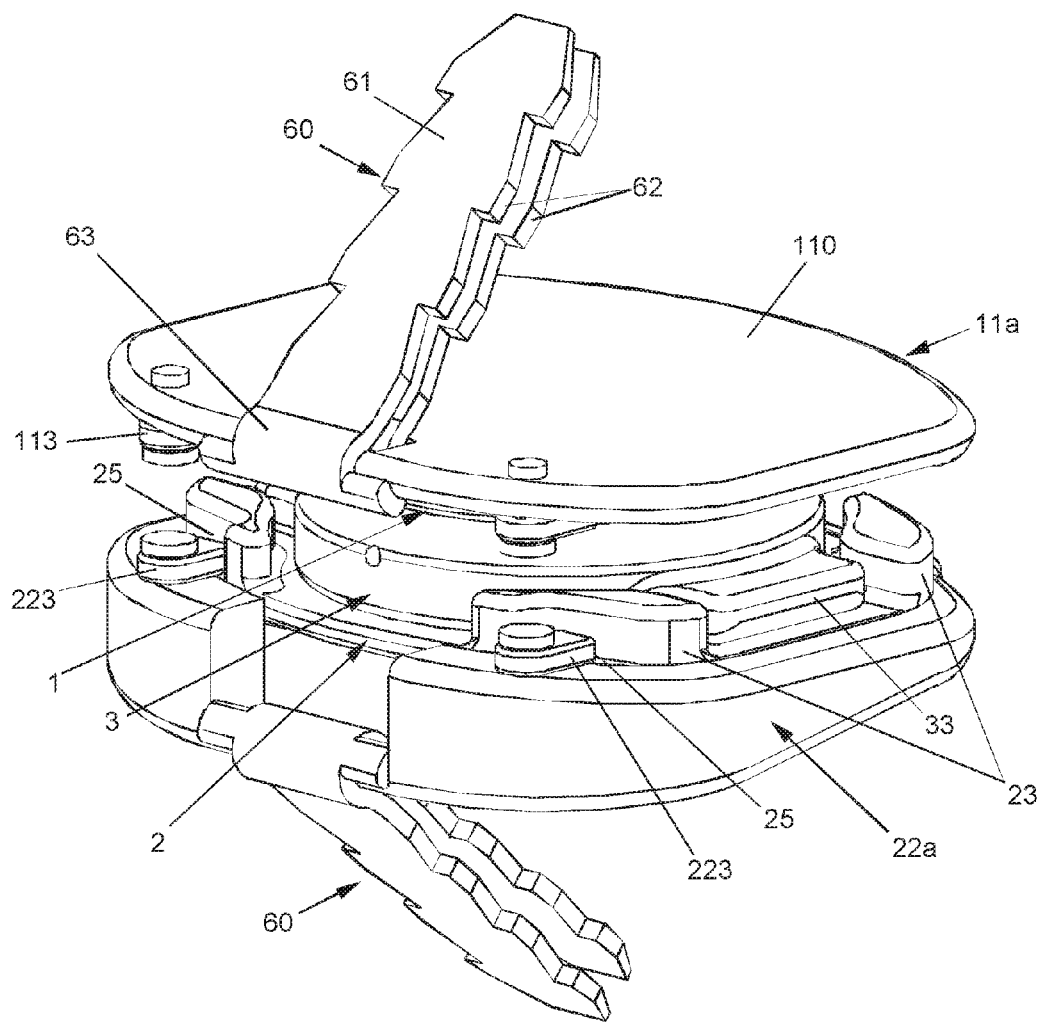
FIG. 3 illustrates a perspective view of the prosthesis according to another embodiment of the invention.

In the embodiment in FIGS. 1 to 3, the core (3) has male cooperation means (33) complementary with female cooperation means (23) present on the lower plate (2). The male cooperation means (33) of the core (3) are, for example, hasps or blocks substantially parallelepiped in shape, present on the side edges of the core (3), as particularly visible in FIGS. 1 to 3. The female cooperation means (23) can consist, for example, of four walls situated, in pairs, on each of the two side edges of the lower plate (2). These walls may, in some cases, be curved to the centre of the prosthesis, so as to cover at least a part of the male cooperation means (33) of the core (3) and avoid lifting the core (3) and the upper plate (1). These cooperation means (23, 33) also prevent the core (3) from ejecting out of the prosthesis, in the event of too much constraint on the prosthesis. In an alternative embodiment, the dimensions of each male cooperation means (33) of the core (3) may be substantially the same as those of each female cooperation means (23) of the lower plate (2), so as to avoid any clearance of the core (3) in relation to the lower plate (2), both in translation and/or in rotation. In the latter case, the only permitted movement of the prosthesis is the inclining of the upper plate (1) in relation to the core (3). In an alternative embodiment, the core (3) has female cooperation means, consisting, for example, of complementary recesses of the male means present on the lower plate (2). These male means of the lower plate (2) may consist, for example, of two blocks or two nibs, curved for example to the interior of the prosthesis and facing one another on two edges of the lower plate (2). The nibs can, for example, be replaced by a block with a bore on which is fixed a hasp by way of a pin penetrating the bore. In another alternative embodiment, the lower plate (2) has half dog points. The core (3), by way of complement, has wells under its lower surface. The dimensions of the half dog points of the lower plate (2) and of the wells of the core (3) will be adapted, by choice, by a slight clearance of the core (3) in translation and in rotation or by no clearance, according to the desired result. In other alternatives, the cooperation means may be located on the core (3) and on the upper plate (1), instead of the lower plate (2). These are just some examples of such means as those of skill will appreciate after understanding this disclosure.

The description of a preferred embodiment will now be considered in reference to FIG. 1. In this embodiment, upper and lower anatomic adaptation elements consist of anatomic plates (11a, 22a), which respectively cover the upper (1) and lower (2) plates. The upper (222a) and lower (111a) surfaces of lower (22a) and upper (11a) anatomic adaptation plates may be reinforced in which respectively the lower (2) and upper (1) plates are housed. In another alternative, these upper (222a) and lower (111a) surfaces of the anatomic adaptation elements can be plane and comprise stoppers which, as for the aforementioned reinforcement, prevent the lower (2) and upper (1) plates respectively from moving in relation to the anatomic adaptation elements. The upper (222a) and lower (111a) surfaces of lower (22a) and upper (11a) anatomic adaptation elements respectively prolong the upper (10) and lower (20) surfaces of the upper (1) and lower (2) plates, to present contact surfaces of the prosthesis with the adjacent vertebrae which are larger than instances in which there are no anatomic adaptation elements (11a, 22a). Different sizes of the anatomic plates of the anatomic adaptation elements (11a, 22a) can be adapted to a single unit created by the two plates (1, 2) and the core (3), to provide contact between the prosthesis and the vertebrae of differing sizes.

In the embodiment of the prosthesis according to the invention illustrated in FIG. 2, anatomic adaptation elements (11b, 22b) consist of crowns which surround upper (1) and lower (2) plates. In this embodiment, the edges of upper (10) and lower (20) surfaces of upper (1) and lower (2) plates are bevelled and complementary with respect to the lower (111b) and upper (222b) inside edges of upper (11b) and lower (22b) crowns, respectively. This inclined shape of the edges of plates (1, 2) and of anatomic adaptation crowns (11b, 22b) cooperates with fixation means (113, 223) of the anatomic adaptation elements to maintain anatomic adaptation crowns (11b, 22b) fixed in the plane of upper (1) and lower (2) plates of the prosthesis, respectively. The anatomic adaptation crowns (11b, 22b) prolong upper (10) and lower (20) surfaces of upper (1) and lower (2) plates, to present contact surfaces of the prosthesis with the adjacent vertebrae which are larger than when there are no anatomic adaptation elements (11, 22). In the same manner as for the aforementioned anatomic plates (11a, 22a), a single unit created by the two plates (1, 2) and the core (3) can thus be adjusted to vertebrae of differing sizes, due to different sizes of crowns (11b, 22b) of the anatomic adaptation elements (11, 22).

In many preferred embodiments, the anatomic adaptation elements (11, 22) may symmetrically or asymmetrically prolong upper (10) and lower (20) surfaces, respectively of upper (1) and lower (2) plates. Thus, for example, the anterior edge of the anatomic adaptation elements (11, 22) may have a larger contact surface with the vertebrae than its posterior edge, so that the center of articulation of the prosthesis (described above) is centered in relation to the natural axis of the spinal column, that meaning off center to the rear of the vertebrae of a ⅔-⅓ section.

Many preferred embodiments, are helpful in the correction of the defects of lordosis. The presence of an angle between the upper and lower surfaces of the prosthesis, in contact with the adjacent vertebrae, is often desirable. Such an angle may be obtained with an upper plate (1), whose median planes representing its lower (14) and upper (10) surfaces create an angle. In other embodiments, lower plate (2) exhibits median planes representing lower (20) and upper (24) surfaces which create an angle. In other embodiments at least one of the anatomic adaptation elements (11, 22) has median planes of the respective structures lower and upper surfaces which create an angle that may be represented by thus, a single unit having two plates (1, 2) and core (3) may be used, for example, to induce or not lordosis, depending on which anatomic adaptation elements (11, 22) are associated with it. In the embodiment illustrated in FIG. 3, lower surface (220) of lower anatomic plate (22a) creates an angle with upper surface (222a). Such an angle which a slightly offset position of the core (3) in relation to the centre of the prosthesis may also be implemented. This slightly offset position of the core (3) may, for example, be maintained with an adjustable positioning of the male and female cooperation means (23, 33). If the surgeon wishes, for example, to induce lordosis within a range of values, a prosthesis may be selected whose core (3) can have slight clearance in translation and in rotation relative to lower plate (2), but about a position imposing a slight permanent inclination of at least one of the plates, due to an accurate adjustment of the cooperation means (23, 33) between core (3) and lower plate (2). Thus, in several preferred embodiments, the median planes representing upper (110, 222a) and lower (111a, 220) surfaces of the anatomic adaptation elements (11, 22) may be substantially parallel or form an acute angle. The inclination obtained by such an angle allows adaptation of the overall shape of the prosthesis to the anatomy of the spinal column or to reduce or correct inclination defects of the vertebrae of the patient for whom the prosthesis is intended. The same anatomic adaptation elements (11, 22) can be assembled with different plates (1, 2) whose upper (10, 24) and lower (14, 20) surfaces create different angles. In other instances, plates (1, 2), whose upper (10, 24) and lower (14, 20) surfaces are parallel, are assembled with anatomic adaptation elements (11, 22) having upper (110, 222a) and lower (111a, 220) surfaces which exhibit different angles. This angle between upper (10) surface of upper plate (1) and lower surface (20) of lower plate (2) may be imposed either by the fact that the median planes representing the lower (20, 14) and upper (24, 10) surfaces of the lower plate (2) and/or the upper plate (1) create an angle, or by restricting, thanks to the cooperation means (23, 33), movements of the core (3) about a position imposing an inclination of at least one of the plates (1, 2).

Illustrated in FIGS. 1 to 3 are movable osseous anchorage means (60) of anatomic adaptation elements (11, 22). Osseous anchorage means (60) may be fixed onto the anatomic adaptation elements (11, 22) upon fixing them onto the plates (1, 2) and/or upon inserting the prosthesis between vertebrae. Thus, the surgeon may easily position the prosthesis between the vertebrae and then insert the osseous anchorage means (60) once the prosthesis has been correctly positioned. In the embodiment presented in FIG. 1, these movable osseous anchorage means (60) consist of a plate (61) equipped with notches (62) oriented to resist removal of plate (61) once it has been inserted into the vertebra. Plate (61) can, of course, be replaced by a rod in the shape of a nail, for example, with or without notches (62) to resist against its removal from the vertebra. A far end of plate (61) bears a part (63) curved to fold over itself. This curved part forms a kind of a hook intended to be interlocked onto an edge (16, 26) of an opening made in the vicinity of the periphery of the anatomic adaptation elements (11, 22). This edge (16, 26) of the opening creates a sort of rod onto which the osseous anchorage means (60) interlock. The curved part (63) allows clasping the osseous anchorage means (60) onto the rod-like edge (16, 26) of anatomic adaptation elements (11, 22). This rod-like edge may be replaced by any equivalent means that attach to the osseous anchorage means (60). In the embodiments illustrated in FIGS. 1 to 9, rod-like edge (16, 26) is located an anterior edge of anatomic adaptation elements (11, 22). This allows the surgeon access after insertion via anterior means (through accessing the vertebrae from their anterior face). If the implanting of the prosthesis is to be done via posterior means, anatomic adaptation elements (11, 22) may have rod-like edge (16, 26) located on the posterior edge. If the implanting of the prosthesis is to be done via lateral means, anatomic adaptation elements (11, 22) may have a rod-like edge (16, 26) located on at least one of their edges. In the embodiment illustrated in FIGS. 2 and 3, hooked part (63), curved to fold over itself, of the notched plate (61) of movable osseous anchorage means (60) of anatomic adaptation crowns (11b, 22b) prolong with a second plate (61) which may be equipped with notches (62) oriented to resist against removal of plate (61) once inserted. In the embodiment illustrated in FIG. 2, second plate (61) is shorter than first plate and in the embodiment illustrated in FIG. 3, it is as long as the first plate. Where osseous anchorage means (60) locks onto the rod-like edge (16, 26) allows it to have a variable angle which facilitates the attaching of the prosthesis. Depending on its encumbrance, the surgeon will have a choice of angles according to which he wishes to drive the osseous anchorage means (60) into the vertebrae. Moreover, because osseous anchorage means (60) may be inserted after positioning the prosthesis between the vertebrae there can be adjustment of the relative position of the different elements (1, 2, 3) of the prosthesis. Inserting the prosthesis generates constraints on the elements of the prosthesis which are movable in relation to each other. Thus, there is a misalignment. The surgeon may, with embodiments hereof, adjust the position of the prosthesis between the vertebrae and adjust the relative position of the elements of the prosthesis between themselves prior to definitively attaching the prosthesis.

Figure 10A:
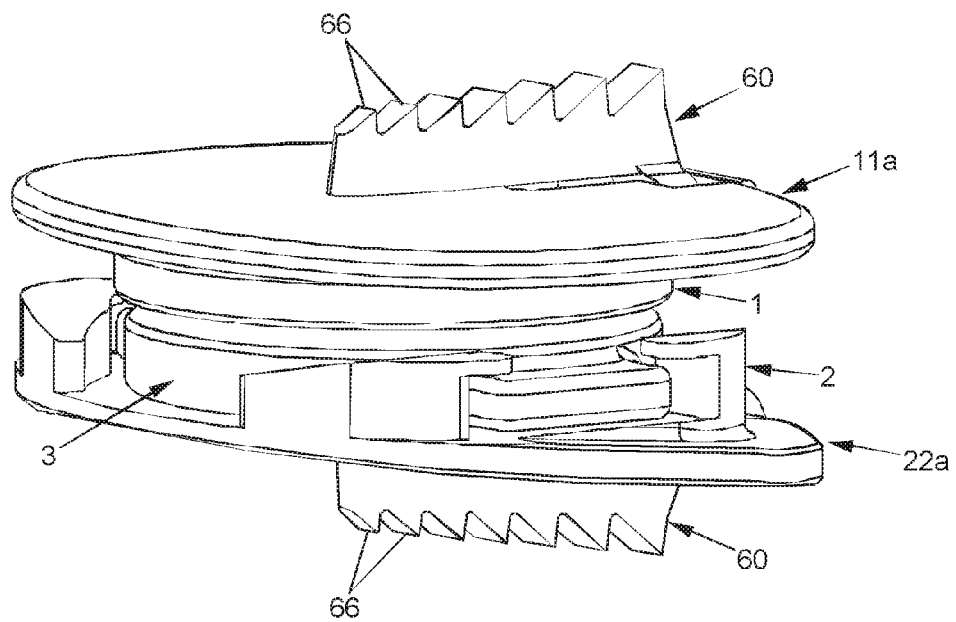
FIGS. 10A and 10B illustrate perspective views of, respectively, the prosthesis comprising osseous anchorage means according to an embodiment of the present invention and one of the osseous anchorage means according this embodiment.
Figure 10B:
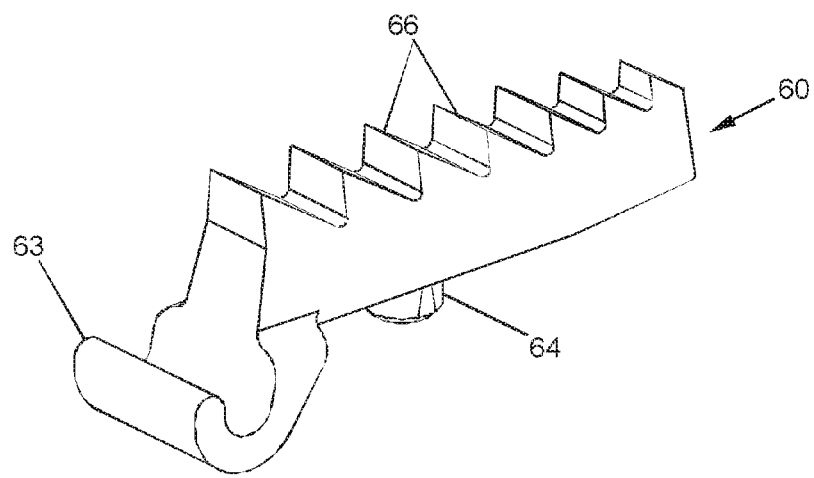
Figure 11A:
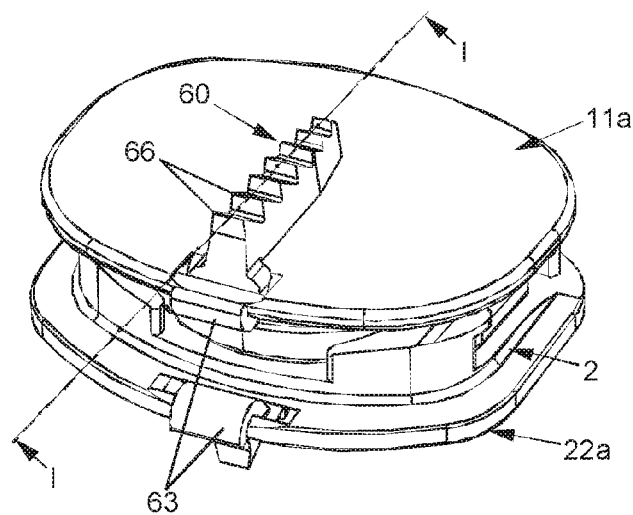
FIGS. 11A and 11B respectively illustrate a perspective view of the prosthesis comprising osseous anchorage means according to an embodiment of the present invention and a cross section view along plane I-I of FIG. 11A.
Figure 11B:
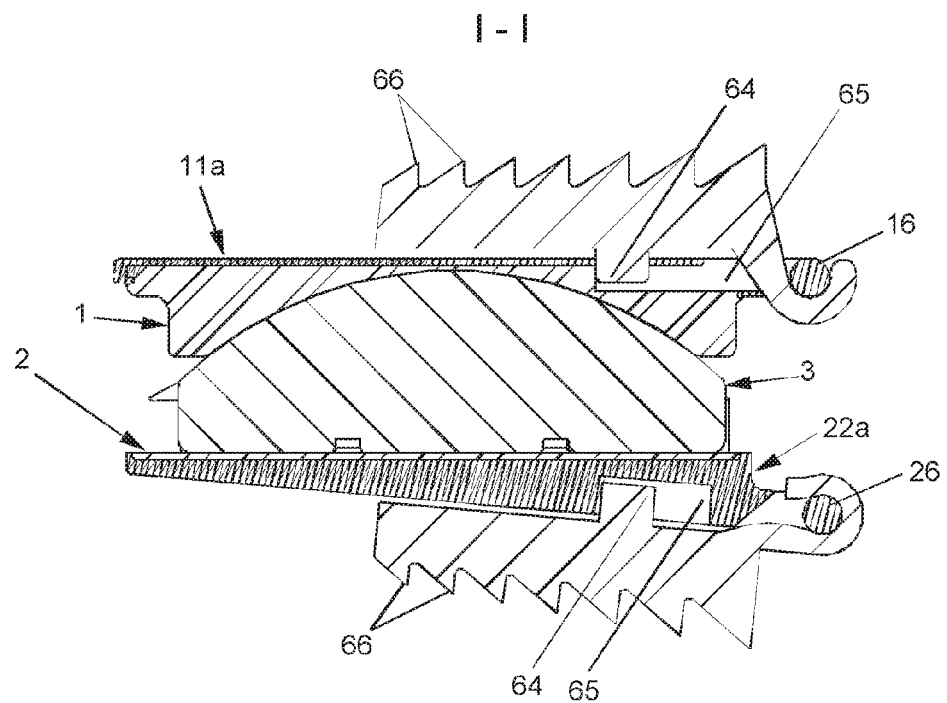

Those of ordinary skill will recognize that the present prosthesis can comprise other osseous anchorage means (60) than those described above, without departing from the scope of the present invention. To give non-limitative examples, such osseous anchorage means (60) can consist of winglets fixed on the prosthesis as in the Patent Application WO03/039400 or of a stud nailed in the vertebra through the anatomic adaptation elements as in the Patent Application WO04/041129. One embodiment of the anchorage means (60) is presented on the FIGS. 10A, 10B, 11A and 11B. Osseous anchorage means (60) according to this embodiment consist of winglets comprising a hooked part (63), curved to fold over itself, so that the winglets can be adapted onto the anatomic adaptation elements. Hooked part (63) of the winglet, particularly visible on FIG. 10B, allows the anchorage means (60) to be interlocked onto the edge (16, 26) of an opening made in the vicinity of the periphery of the anatomic adaptation plates (11a, 22a), as particularly visible on FIGS. 11A and 11B. This edge (16, 26) of the opening creates a sort of rod onto which the osseous anchorage means (60) interlock, as described above. The winglet further comprises a pin (64) (or a dowel) adapted to be inserted into a groove (65) present on the surface of the plate and/or the anatomic adaptation element on which the winglet is to be fixed, as particularly visible on FIG. 11B. The groove (65) and the pin (64) have dimensions adapted so that the pin (64) is secured into groove (65). For example, pin (64) may have a substantially conical shape, with the larger diameter of the cone being at the base of the pin and the smaller diameter being at its end. Groove (65) may have side walls adapted to cooperate with the conical shape of the pin (64) so that the pin tightly fits inside the groove and thus secures the osseous anchoring means (60) onto anatomic adaptation plates (11a, 22a). For example, the width of the groove (65) may be larger at its surface than at its bottom. The osseous anchorage means (60) are thus fixed onto the prosthesis by first interlocking hooked part (63) onto rod-like edge (16, 26) of anatomic adaptation plates (11a, 22a) and by rotating osseous anchorage means (60) the rod until pin (64) penetrates into groove (65) of anatomic adaptation plate (11a, 22a) and/or of plate (1, 2). Winglet (60) may have a standard size for many of the embodiments and the position of pin (64) of winglet (60) inside groove (65) may vary as a function of the size of anatomic adaptation plates (11a, 22a). Depending on the thickness of anatomic adaptation plates (11a, 22a), pin (64) penetrates into anatomic adaptation plates (11a, 22a) or may traverse anatomic adaptation plates (11a, 22a) and penetrate into a groove (65) in plates (1, 2), as shown for example on FIG. 11B for upper plate (1). Since the anatomic adaptation plates (11a, 22a) may vary in size (diameter), their groove may have variable lengths and can be replaced by a hole having a variable distance from the rod-like edge (16, 26) so that the hole is adapted to receive the pin (64). When the pin is designed to penetrate the plates also, the plates will typically include a groove because the distance of the pin from the periphery of the plates will vary depending on the size of the anatomic adaptation plates (11a, 22a). Once secured onto the anatomic adaptation plates (11a, 22a), winglets (60) are adapted to cooperate with a groove drilled in the surfaces of the adjacent vertebrae with which they are in contact. Thus, the surgeon may create a groove in the surfaces of vertebrae between which the prosthesis is intended to be inserted. This groove in the vertebrae may have an orientation relative to the sagittal plane that will depend on the position and orientation of the winglet. This orientation may be predetermined and may then set and secure the orientation of the prosthesis. Similarly, the depth of the groove in the vertebrae and its extend from the periphery will be predetermined as a function of the size of winglet (60) and may allow the surgeon to adjust the relative position of the various elements of the prosthesis and predict the position of the prosthesis relative to the natural axis of the vertebrae. The winglets typically comprise notches (66) on their surfaces which are intended to be in contact with the bottom of the groove preformed in the vertebrae. Notches (66) of winglets (60) will resist against the ejection of the prosthesis from inside its housing between the vertebrae, such as for example when strong constraints are applied to the prosthesis. With reference to FIG. 11B, hooked part (63) of the winglets (60) can be oriented so that they are to be interlocked onto the rod-like edge (16, 26) by being inserted inside the opening made in the vicinity of the periphery of the anatomic adaptation plates (11a, 22a) or by being inserted from outside this opening.

The osseous anchoring means (60) described above are adapted to anatomic adaptation plates (11a, 22a) but may also be adapted to anatomic adaptation crowns (11b, 22b) comprising an opening in the vicinity of their periphery or to the plates of other types of intervertebral disc prosthesis having plates comprising an opening in the vicinity of their periphery. The edge (16, 26) of such opening in the plates create a sort of rod onto which the hooked part (63) of both removable embodiments of the osseous anchoring means (60) can be interlocked.

FIGS. 4 to 9 illustrate plates (1, 2) of the prosthesis traverse equipped with anatomic adaptation elements (11, 22) and illustrate different exemplar embodiments of fixation means (113, 223, 15, 25) of these anatomic adaptation elements (11, 22) on plates (1, 2). Fixation means (113, 223, 15, 25) are in some embodiments, reversible, this means that anatomic adaptation elements (11, 22) can be attached and removed from plates (1, 2) of the prosthesis. Fixation means (113, 223, 15, 25) thus allow anatomic adaptation elements (11, 22), fixable in a moveable manner to plates (1, 2), to be changed. Fixation means (113, 223, 15, 25) of anatomic adaptation elements (11, 22) on plates (1, 2) consist of fixation means (113, 223) present on anatomic adaptation elements (11, 22) and complementary with fixation means (15, 25) present on the plates (1, 2) of the prosthesis. Anatomic adaptation elements (11, 22) are fixed onto plates (1, 2) via, contact of at least a part of their lower (111) face (which, for example, may be lower surfaces 111a or lower edges 111b) and upper (222) face (which, for example, may be upper surfaces 222a or upper edges 222b) with at least a part upper (1) and lower (2) plates and, on the other hand, contact of their fixation means (113, 223) with complementary fixation means (15, 25) present on plates (1, 2) of the prosthesis. For anatomic plates (11a, 22a) such as those illustrated, for example, in FIGS. 4A to 4D, anatomic adaptation elements (11, 22) are fixed onto plates (1, 2) with upper (10) and lower (20) surfaces of upper (1) and lower (2) plates which are attached to reinforcements present on lower (111a) and upper (222a) surfaces respectively of the upper (11) and lower (22) anatomic plates, via fixation means (113, 223, 15, 25). For anatomic crowns (11b, 22b) such as those illustrated, for example, in FIGS. 5A to 5C, anatomic adaptation elements (11, 22) are fixed onto plates (1, 2) with bevelled parts of upper (10) and lower (20) surfaces, respectively of upper (1) and lower (2) plates which are attached to bevelled parts of upper (111b) and lower (222b) edges of upper (11) and lower (22) anatomic crowns, via fixation means (113, 223, 15, 25). Different embodiments of fixation means (113, 223, 15, 25) of anatomic adaptation elements (11, 22) on plates (1, 2) will now be described in reference to FIGS. 4 to 9. These fixation means are given by way of illustration and can be replaced by other means such as will be recognized by those of skill. A variety of combinations of the different fixation means (113, 223, 15, 25) are described below.

In several embodiments, fixation means (113, 223, 15, 25) of anatomic adaptation elements (11, 22) on plates (1, 2) consist of male fixation means (113, 223) present on anatomic adaptation elements (11, 22) and cooperate with female fixation means (15, 25) present on plates (1, 2) of the prosthesis. Female fixation means (15, 25) present on plates (1, 2) of prosthesis can consist, for example, in plane surfaces (15, 25) present on edges of plates (1, 2) of the prosthesis or in recesses (15, 25) either made in the edges of the plates (1, 2) of the prosthesis, or in the edges of female cooperation means (23) of plates (1, 2) of the prosthesis.

Figure 4A:
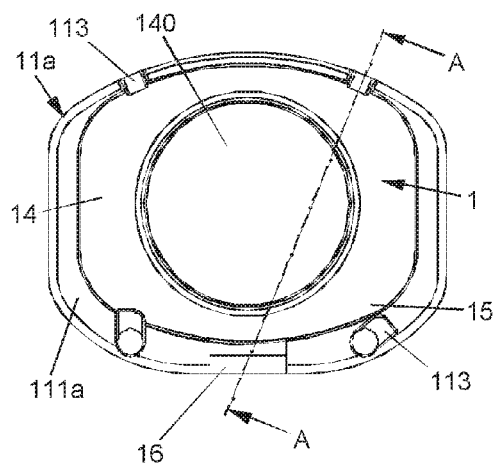
FIGS. 4A and 4B respectively illustrate a bottom view and a cross section view along plane A-A in FIG. 4A, of the upper plate equipped with its anatomic adaptation element, according to an embodiment of the invention, FIGS. 4C and 4D respectively illustrate a plan view and a cross section view along plane B-B in FIG. 4C, of the upper plate equipped with its anatomic adaptation element, according to an embodiment of the invention.
Figure 4B:
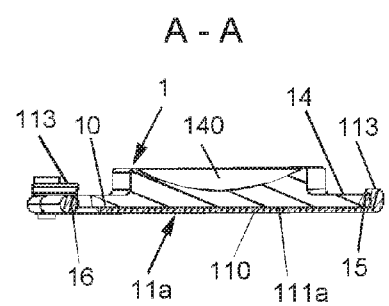
Figure 4C:
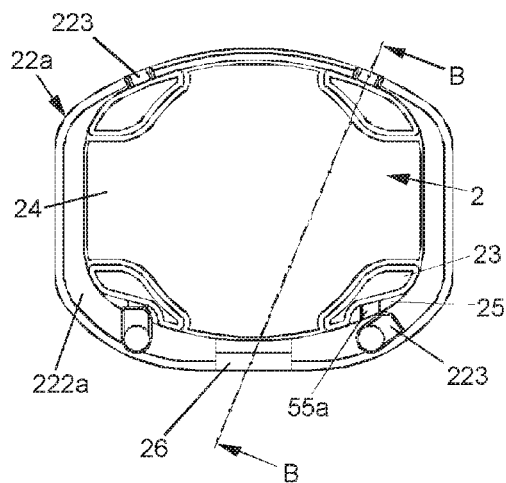
Figure 4D:
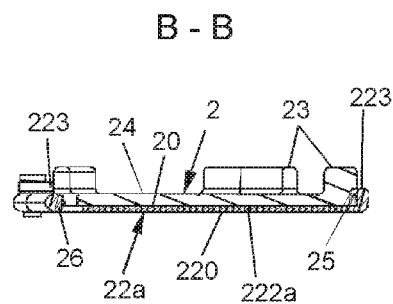

In an embodiment illustrated in FIGS. 4A and 4B, fixation means (113) of upper anatomic plate (11a) consist, on posterior edge of lower surface (111a), in nibs which are shaped and have dimensions intended to receive a section (15) of posterior edge of lower surface (14) of upper plate (1). On an anterior edge of its lower surface (111a), fixation means (113) of upper anatomic plate (11a) consists in latches constituted in an axis of rotation onto which a hasp is mounted to swivel about this axis and receive a section (15) of posterior edge of lower surface (14) of upper plate (1), as shown in FIGS. 4A and 4B. Right-hand latches in FIGS. 4A to 4C are illustrated in the open position and the left-hand latches are in the closed position. In the embodiment illustrated in FIGS. 4C and 4D, fixation means (223) of lower anatomic plate (22a) consist, on the posterior edge of lower surface (222a), in nibs which are shaped and have dimensions to fit into opening (25) made in cooperation means (23) of lower plate (2). On anterior edge of its lower surface (222a), fixation means (223) of upper anatomic plate (22a) consist of latches constituted in an axis of rotation onto which a hasp is mounted intended to receive a recess (25) made in a part of cooperation means (23) present on posterior edge of the lower plate (2). Latches illustrated in FIGS. 4A to 4D can be maintained in the closed position via securing means (55) present, for example, on plates (1, 2) of the prosthesis. For example, as illustrated in FIG. 4C, a notch (55a) made on recess (25) present on a part of the cooperation means (23) of the lower plate (2) prevents latch (223) of lower anatomic plate (22a) from swiveling.

Figure 5A:
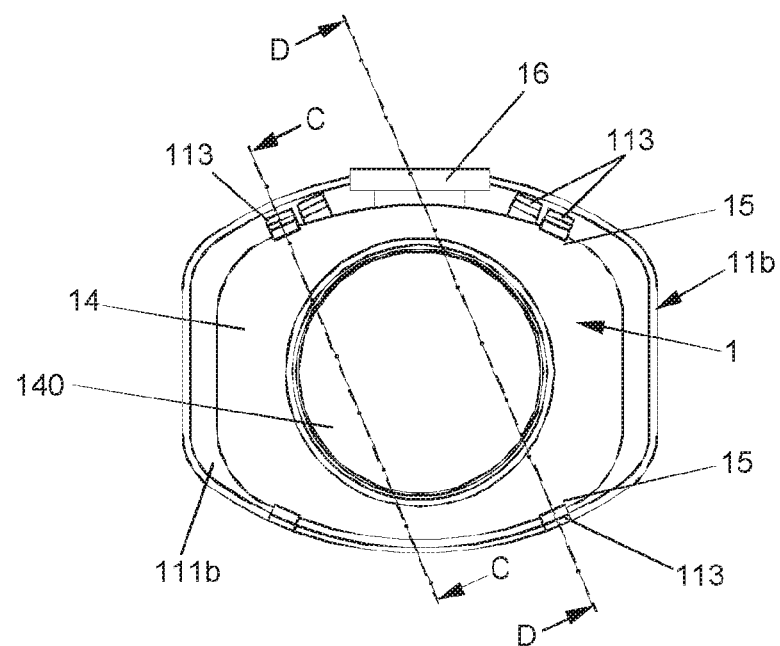
FIG. 5A illustrates a bottom view of the upper plate equipped with its anatomic adaptation element, according to an embodiment of the invention.
Figure 5B:
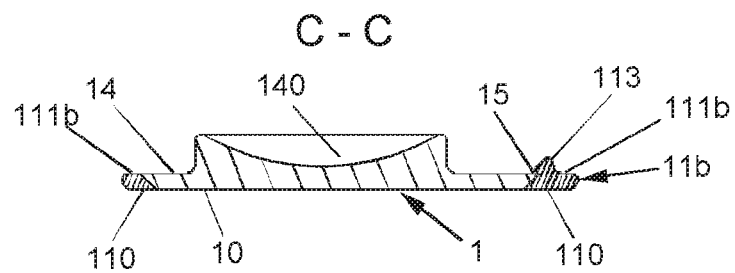
FIGS. 5B and 5C illustrate cross section views respectively along plane C-C and plane D-D in FIG. 5A, of the upper plate equipped with its anatomic adaptation element, according to this embodiment of the invention.
Figure 5C:
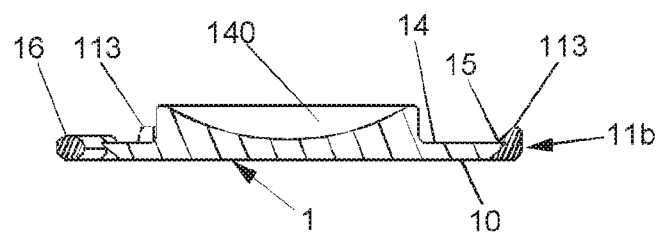

In the embodiment in FIGS. 5A to 5C, anterior and posterior edges of the upper anatomic adaptation crowns (11b) have fixation means (113) consisting in nibs which cooperate with a plane section (15) present on the edge of the lower surface (14) of the upper plate.

In the embodiments in FIGS. 6A to 9D, fixation means (113, 223, 15, 25) of anatomic adaptation elements (11, 22) on plates (1, 2) consist in female fixation means (113, 223) present on anatomic adaptation elements (11, 22) and co-operating with male intermediary means (50) which can also cooperate with female fixation means (15, 25) present on plates (1, 2) of the prosthesis. Anatomic adaptation elements (11, 22) are fixed onto plates (1, 2) via, contact of at least a part of their upper (111) and lower (222) faces with at least a part, respectively of the upper (1) and lower (2) plates and, on the other hand, contact of male intermediary means (50) with female fixation means (113, 223) present on anatomic adaptation elements (11, 22) and with female fixation means (15, 25) present on plates (1, 2) of the prosthesis. Male intermediary means (50) consist in a sliding plate (50) in female fixation means (113, 223) present on anatomic adaptation elements (11, 22) to cooperate with female fixation means (15, 25) present on plates (1, 2) of prosthesis. Plate (50) is substantially parallelepiped in shape and can comprise, on its side edges, fins (500), particularly visible, for example, in FIG. 7A. Fins (500) of the male intermediary means (50) are of complementary shape with female fixation means (113, 223) of anatomic adaptation elements (11, 22) and with female fixation means (15, 25) of plates (1, 2) of prosthesis, which have side runners in which these fins (500) slide. This complementary shape of the fins (500) of the plate (50) and the runners of the female fixation means (113, 223) of anatomic adaptation elements (11, 22) as well as the female fixation means (15, 25) of plates (1, 2) prevent plate (50) from leaving these female fixation means (113, 223, 15, 25) prior to being secured via the securing means (55).

Male intermediary means (50) have securing means (55) blocking the male intermediary means (50) in the position where they cooperate with both the female fixation means (113, 223) of the anatomic adaptation elements (11, 22) and with the female fixation means (15, 25) present on the plates (1, 2) of the prosthesis. Securing means (55) which consist, for example, in at least an irregularity (for example, notches 55a, slots 55b, or other variants) present on at least one side of plate (50) and to cooperate with at least an opening (550) made in female fixation means (113, 223) of anatomic adaptation elements (11, 22) and/or in female fixation means (15, 25) of plates (1, 2). Opening (550) can be of a complementary shape of male intermediary means (50) or of its securing means, as illustrated in FIGS. 6A and 6B.

Figure 6A:
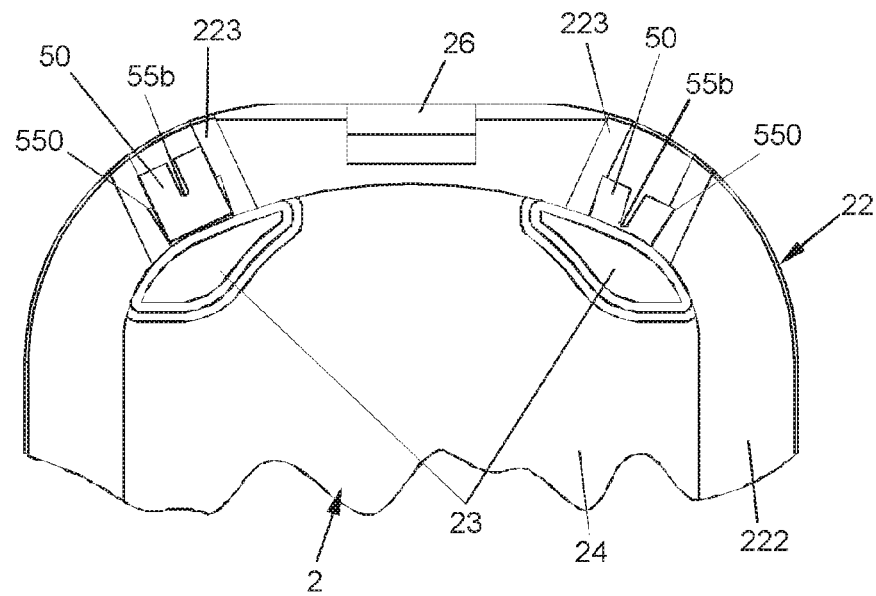
FIGS. 6A and 6B illustrate bottom views of a part of the upper plate equipped with its anatomic adaptation element, according to two different embodiments of the invention.
Figure 6B:
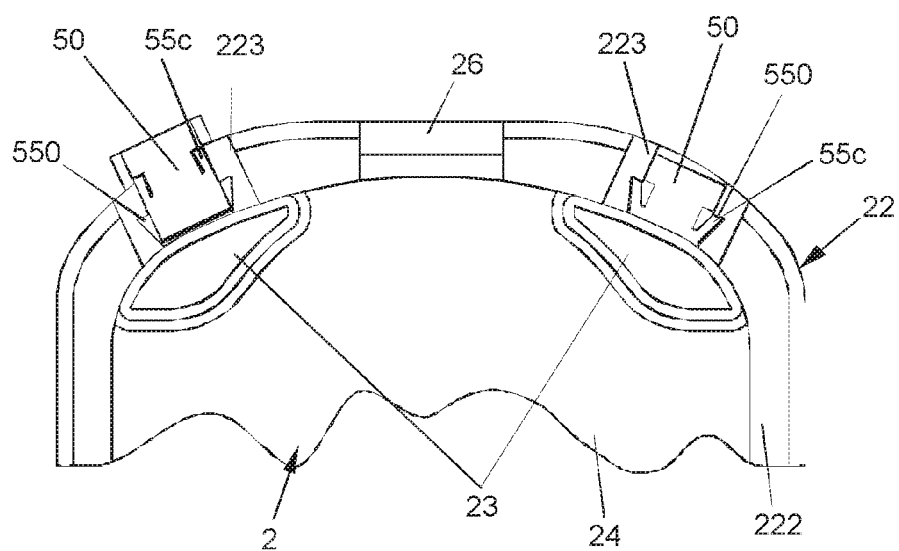

In the embodiment illustrated in FIG. 6A, the plate constituting male intermediary means (50) widens out towards its posterior end and the irregularity constituting the exemplar securing means (55) comprises a slot (55b) on the posterior half of the plate (50). This slot (55b) compresses the posterior end of the plate (50) when it is introduced into the female fixation means (113, 223) of the upper and/or lower anatomic adaptation elements (11, 22), as illustrated for the left-hand plate in FIG. 6A. When plate (50) reaches its end of stroke in the runner created by the female means (113, 223) of anatomic adaptation elements (11, 22) and means (15, 25) of plates (1, 2), meaning when it cooperates with these two female means at the same time, openings (550) made, for example, in the female means (113, 223) of the anatomic adaptation elements (11, 22) separate the plate

Figure 7A:
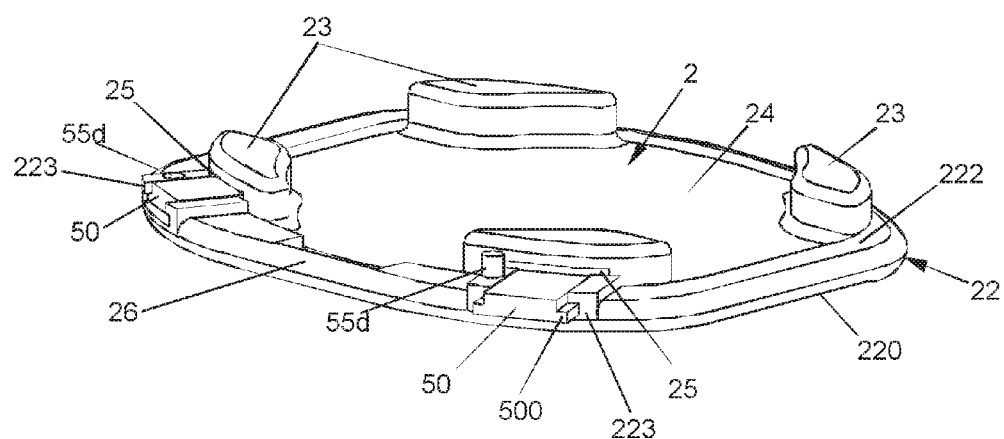
FIGS. 7A and 7B illustrate perspective views of the lower plate equipped with its anatomic adaptation element, according to two different embodiments of the invention.
Figure 7B:
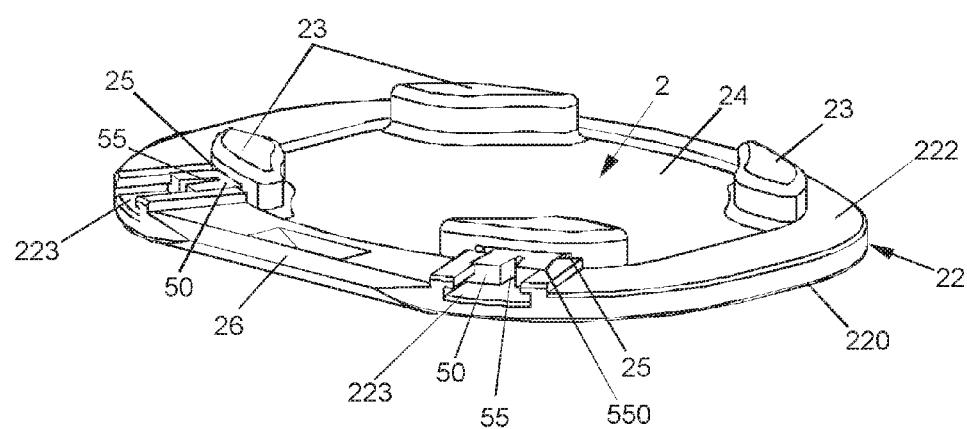

(50) from its hold. This is illustrated for the right-hand plate in FIG. 6A. FIG. 7B illustrates a perspective view of this embodiment of fixation means in which plate (50) is intended to be held in female manes (25) made in cooperation means (23) of lower plate (2). This figure also shows the reinforcement present, for example, on lower anatomic plate (22a) may be deeper than the thickness of the lower plate (2). Depending on the size of cooperation means (23, 33) of lower plate (2) of core (3), the edges of this reinforcement may provide a periphery abutment possibly limiting the displacement of core (3) in relation to lower plate (2). In the embodiment illustrated in FIG. 6B, irregularities constituting securing means (55) of male intermediary means (50) consist in hasps present on the side edges of the plate (50). As illustrated for left-hand plate (50) in FIG. 6B, these hasps (55c) are compressed when hasp is introduced into the runners of female means (113, 223). When the plate is pushed as far as the blocking position, hasps (55c) open out in openings (550) provided for on the side edges of the female means (113, 223) of upper and/or lower anatomic adaptation elements (11, 22), as illustrated for right-hand plate (50) in FIG. 6B.

Figure 8A:
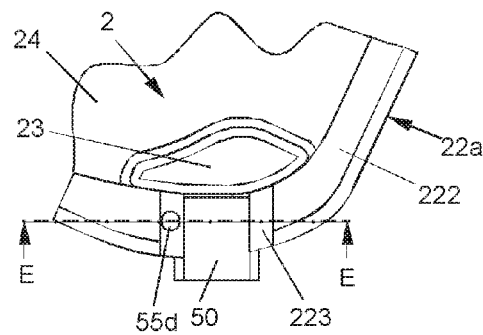
FIGS. 8A and 8B respectively illustrate a bottom view and a cross section view along plane E-E in FIG. 8A, of a part of the lower plate equipped with its anatomic adaptation element whose fixation means are open, according to an embodiment of the invention, FIGS. 8C and 8D respectively illustrate a bottom view and a cross section view along plane F-F in FIG. 8C, of the same embodiment as in FIGS. 8A and 8B, but with the fixation means of the anatomic adaptation element closed and locked, according to an embodiment of the invention.
Figure 8A:
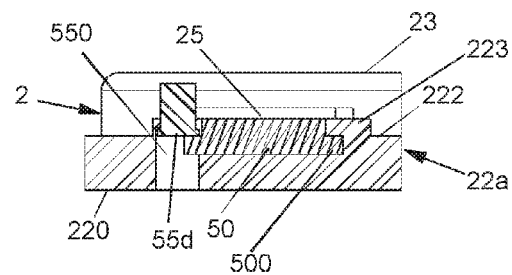
Figure 8C:
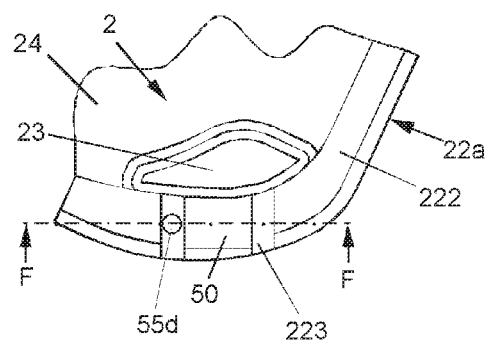
Figure 8C:
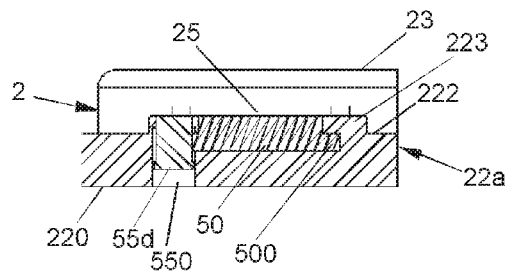

FIGS. 7A and 8A to 8D illustrate another alternative embodiment of the male intermediary means (50). In this embodiment, irregularities of plate (50) constituting the securing means (55) of plate (50) consist in a bore in male intermediary means (50), prolonged by a bore (550) in female fixation means (113, 223) of anatomic adaptation elements (11, 22), as particularly visible in FIG. 8B. The bore (550) is intended to receive a securing pin (55d) blocking the male intermediary means (50) in the position where they cooperate with female fixation means (15, 25) present on the plates (1, 2) of prosthesis, as illustrated in FIG. 8C.

Figure 9A:
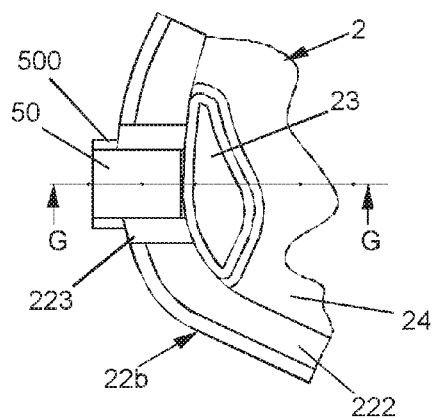
FIGS. 9A and 9B respectively illustrate a bottom view and a cross section view along plane G-G in FIG. 9A, of a part of the lower plate equipped with its anatomic adaptation element whose fixation means are open, according to an embodiment of the invention, FIGS. 9C and 9D respectively illustrate a bottom view and a cross section view along plane H-H in FIG. 9C, of the same embodiment as in FIGS. 9A and 9B, but with the fixation means of the anatomic adaptation element closed and locked, according to an embodiment of the invention.
Figure 9B:
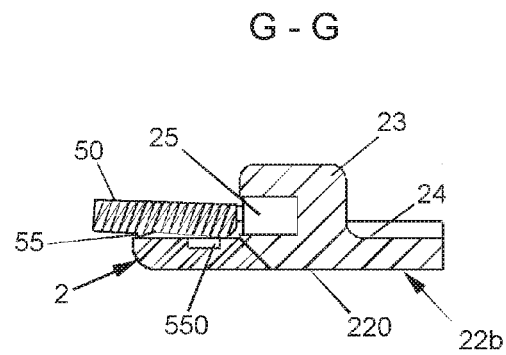
Figure 9C:
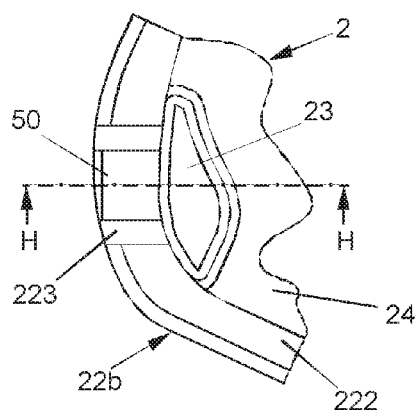
Figure 9D:
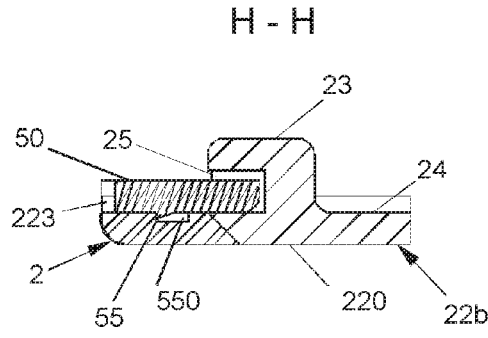

Another alternative of the securing means (55) of male intermediary means (50) is illustrated in FIGS. 9A to 9D. In this alternative, the irregularities constituting securing means (55) of plate (50) consist of a notch (55a) present on the lower surface of the plate and cooperative with an opening (550) made in the female fixation means (113, 223) of anatomic adaptation elements by resisting against removal of plate (50), once driven as far as the female fixation means (15, 25) of the plates (1, 2), as illustrated in FIG. 9D.

It will be evident to those of ordinary skill that the invention allows embodiments in numerous other specific forms without departing from the scope of the invention. The embodiments are offered, therefore, only to illustrate rather than limit the invention which is limited only by the following claims:

The invention claimed is:

1. An intervertebral disc prosthesis comprising at least three pieces including an upper plate, a lower plate, and a core, at least one of the plates and the core being configured for movement of the core at least in translation at least in relation to said at least one of the plates according to an axis substantially parallel to that plate when the prosthesis is assembled, characterized in that the intervertebral disc prosthesis comprises two anatomic adaptation elements of which each has, on one hand, a surface configured for contact with a surface of a vertebra and, on the other hand, a face of which at least a part has a surface in contact with at least a part of the plate opposite to which the anatomic adaptation element is mounted, the anatomic adaptation elements being fixed onto the plates via fixation means; wherein male and female cooperation means situated in the vicinity of the edges of at least one plate and the core limit the movements in translation of the core relative to this plate, according to an axis substantially parallel to this plate, and limit the movements in rotation of the core relative to this plate, about an axis substantially perpendicular to this plate;

the cooperation means of the plate are female cooperation means co-operating with male cooperation means of the core;

the fixation means of the anatomic adaptation elements on the plates comprise male fixation means present on the anatomic adaptation elements and complementary and co-operating with female fixation means present on the plates of the prosthesis; and the female fixation means present on the plates of the prosthesis comprise recesses made in the edges of the female cooperation means of the plates of the prosthesis.

2. An intervertebral disc prosthesis comprising:
an upper prosthesis plate;
a lower prosthesis plate having a peripheral edge and a lower surface;
a lower anatomic adaptation plate having a lower surface configured for contact with a vertebral endplate and an opposite upper surface configured for contact with at least a part of the lower surface of lower prosthesis plate;
a receptacle for a latch plate; and
a latch plate linearly translatable in a direction generally parallel to the upper surface of the lower anatomic adaption plate from a first position in which the latch plate is disposed within the latch receptacle to hold the lower prosthesis plate to the lower anatomic adaptation plate, to a second position in which the latch plate is disposed out of the latch receptacle to release the lower prosthesis plate from the lower anatomic adaptation plate.

3. The intervertebral disc prosthesis of claim 2 further comprising a housing sized to receive the latch plate and allow linear translation of the latch plate from the first position to the second position.

4. The intervertebral disc prosthesis of claim 3 further comprising a fin disposed on the latch plate and extending in the direction of linear translation of the latch plate from the first position to the second position, the fin engagable with a runner disposed in the housing.

5. The intervertebral disc prosthesis of claim 3 further comprising a lock having an engaged position in which the latch plate is blocked in the first position and a released position in which latch plate is movable to the second position.

6. The intervertebral disc prosthesis of claim 5 in which the lock comprises a pin deployed in the housing and slot disposed along an edge of the latch plate in which the pin is receivable when the lock in is the engaged position.

7. The intervertebral disc prosthesis of claim 5 in which the lock comprises a hasp disposed along an end of the latch plate and deployable from a released position in which the latch plate is linearly translatable in the housing to an engaged position in which the hasp expands into a recess disposed in the housing to limit translation of the latch plate and block the latch plate in the first position.

8. The intervertebral disc prosthesis of claim 5 in which the lower anatomic adaptation plate prolongs a surface of the lower prosthesis plate differentially around the peripheral edge of the lower prosthesis plate.

9. An intervertebral disc prosthesis comprising:
an upper prosthesis plate, a lower prosthesis plate having a peripheral edge, and a core comprising a curved surface configured to permit articulation of the upper and lower prosthesis plates and a flat surface configured to permit translation of the core with respect to one of the upper and lower prosthesis plates;
a lower anatomic adaptation plate having a lower surface configured for contact with a vertebral endplate and an opposite upper surface configured for contact with at least a part of the lower prosthesis plate; and
a latch hasp selectively rotatable in a plane generally parallel to the upper surface of the lower anatomic adaption plate from a first position in which the latch hasp retains a first side of the lower prosthesis plate to the lower anatomic adaptation plate, to a second position in which the latch hasp releases the lower prosthesis plate from the lower anatomic adaptation plate.

10. The intervertebral disc prosthesis of claim 9 further comprising an upper anatomic adaption plate having an upper surface configured for contact with a vertebral endplate and an opposite lower surface configured for contact with at least a part of the upper prosthesis plate.

11. The intervertebral disc prosthesis of claim 10 further comprising means for fixing the upper anatomic adaption plate to the upper prosthesis plate.

12. The intervertebral disc prosthesis of claim 9 further comprising a fixed nib that retains a second side of the lower prosthesis plate to the lower anatomic adaptation plate, with the second side of the lower prosthesis plate disposed on a side of the lower prosthesis plate opposite the first side of the lower prosthesis plate.

13. The intervertebral disc prosthesis of claim 12 further comprising a detent notch configured to receive the hasp and retain the hasp in the first position.

14. The intervertebral disc prosthesis of claim 13 in which the lower anatomic adaptation plate prolongs a surface of the lower prosthesis plate equally around the peripheral edge of the lower prosthesis plate.

15. The intervertebral disc prosthesis of claim 13 in which the lower anatomic adaptation plate prolongs a surface of the lower prosthesis plate differentially around the peripheral edge of the lower prosthesis plate.

* * * * *